United States Patent [19]

Sherman

[11] 4,190,886
[45] Feb. 26, 1980

[54] DERIVATION OF STEADY VALUES OF BLOOD PRESSURES

[75] Inventor: Allan P. Sherman, Lexington, Mass.

[73] Assignee: Hewlett-Packard Company, Palo Alto, Calif.

[21] Appl. No.: 894,679

[22] Filed: Apr. 10, 1978

[51] Int. Cl.$^2$ ............................ G06F 15/00; A61B 5/04
[52] U.S. Cl. .................................... 364/415; 364/574; 128/673; 128/681; 128/900
[58] Field of Search ............... 364/417, 415, 416, 574, 364/575, 572; 128/2.05 Q, 2.1R

[56] References Cited

U.S. PATENT DOCUMENTS

| | | |
|---|---|---|
| 3,484,591 | 12/1969 | Trimble .................................. 364/574 |
| 3,506,813 | 4/1970 | Trimble .................................. 364/574 |
| 3,557,354 | 1/1971 | Trimble .................................. 364/574 |
| 3,648,688 | 3/1972 | O'Hanlon, Jr. et al. ......... 364/417 X |
| 3,771,167 | 11/1973 | Ross .................................. 364/575 X |
| 3,848,586 | 11/1974 | Suzuki et al. .................. 364/574 X |
| 3,927,309 | 12/1975 | Fujiwara et al. ..................... 364/574 |
| 3,996,926 | 12/1976 | Birnbaum .......................... 364/416 X |
| 4,009,709 | 3/1977 | Link et al. ...................... 364/415 X |

Primary Examiner—Edward J. Wise
Attorney, Agent, or Firm—Donald N. Timbie

[57] ABSTRACT

Apparatus for deriving an average of data points in which the contribution of each data point to the average is generally inversely related to the difference between its amplitude and the amplitudes of a few previous data points.

10 Claims, 13 Drawing Figures

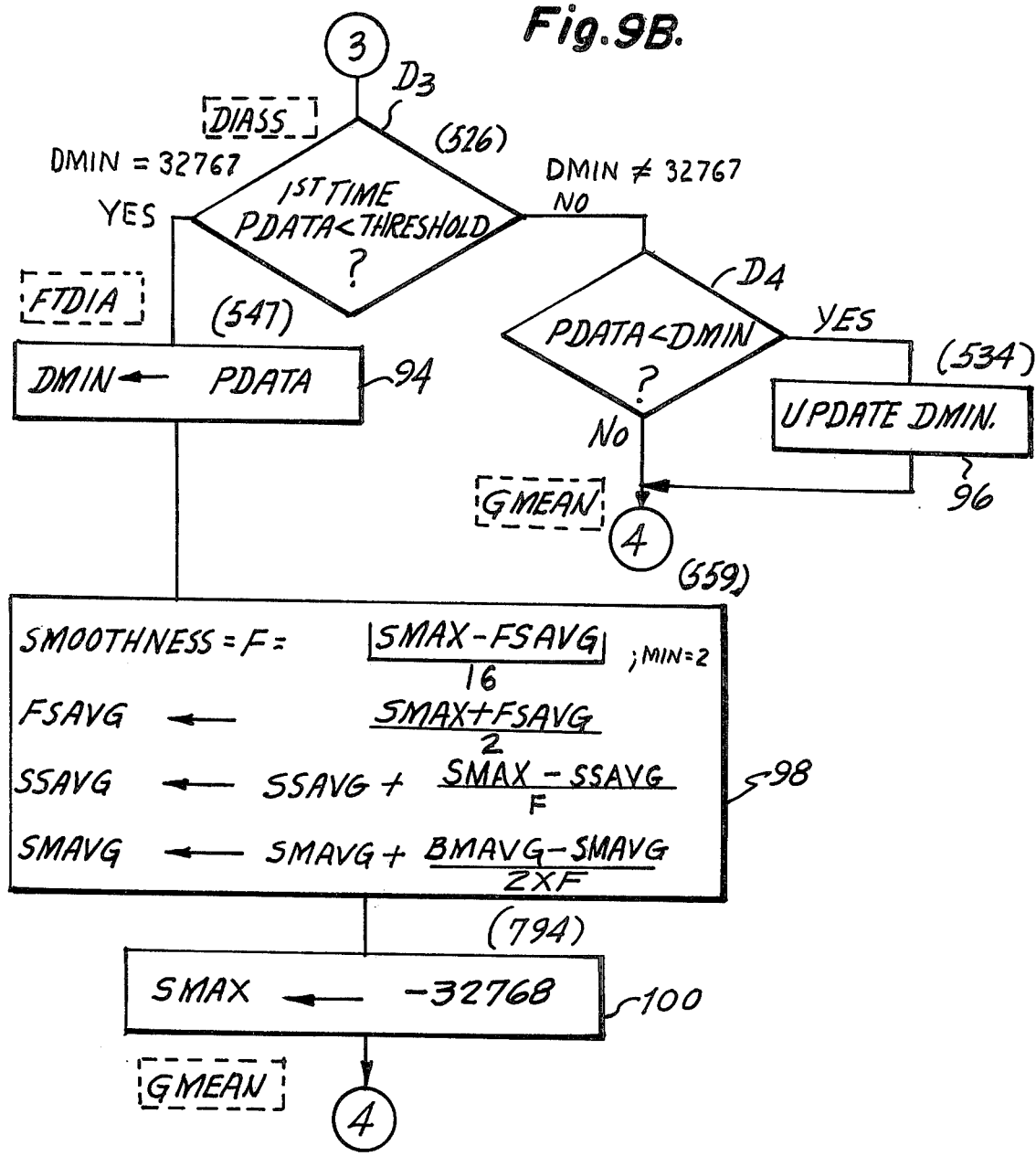

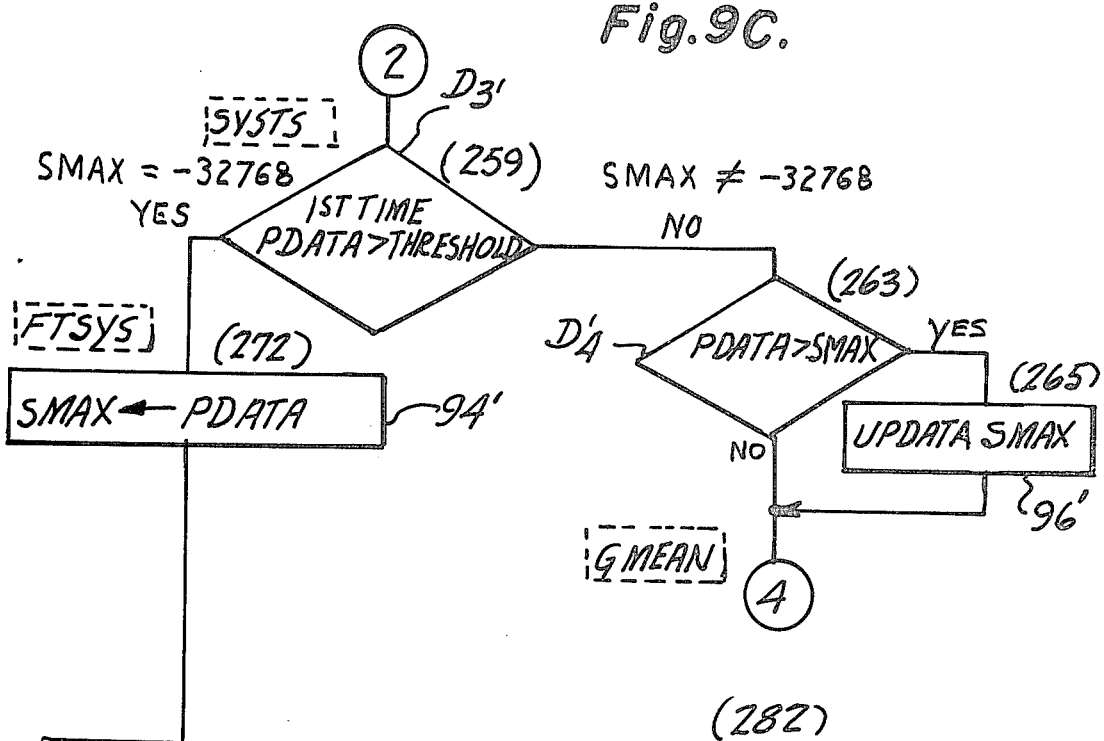

DERIVATION OF STEADY VALUES OF BLOOD PRESSURES

BACKGROUND OF THE INVENTION

In monitoring the systolic and diastolic blood pressure of a patient by directly measuring the pressures of the maximum and minimum peaks of the blood pressure signal, the presence of equipment noise can cause fluctuations in the peak pressures that are not physiological in origin, and the presence of variations in the pressure of the thoracic cavity due to respiration can cause the peak values to slowly undulate. If the peak values are displayed on a strip chart recording or the like, the effects of such changes in their values can be discounted by the careful analysis of a skilled observer, but it is often desired to avoid the need for such analysis by displaying the systolic and diastolic values in numerical form. Fluctuations in the numerically displayed peak values would make it difficult for even a skilled observer to determine the useful systolic and diastolic pressures. This can be even more difficult if pulmonary artery pressures are being monitored because the amplitude of the undulation in pressure due to respiration can be comparable to the pulmonary artery pressures being measured.

Steady values of the systolic and diastolic blood pressures can be derived by respectively applying the fluctuating maximum and minimum peak values to suitable low pass filters, but the systolic and diastolic values derived in this manner are as much affected by peaks of noise as by peaks representing heart action. Furthermore, if the upper limit of the filter is low enough to attenuate the slow fluctuation in the peak values due to respiration, the response may be too slow to reveal sudden changes in the peak levels that are of physiological significance.

BRIEF DISCUSSION OF THE INVENTION

Although this invention will be described and illustrated as it would be used in deriving values of systolic and diastolic blood pressures from a blood pressure signal in such manner that the values are relatively free from the effects of artifacts and respiration, it can be used to derive a stable indicator of the level of any signal that changes more slowly than undesired perturbations. While this indicator responds quickly to sustained changes in the nature of the signal, it is relatively insensitive to spurious artifacts. Furthermore, the indicator is an average of the signal in which each constituent portion of the signal affects the average in a generally inverse relationship to the amount of its variation from the immediately preceding constituents of the signal. The immediately preceding constituents can be the portion of the signal occurring within a predetermined prior period, the portion of the signal represented by a predetermined number of samples, or an exponential average of the entire previous signal whether it be continuous or represented by samples.

However the maximum and minimum peaks of the blood pressure signal may be detected, the systolic and diastolic values to be displayed are derived from them in accordance with the invention in such manner as to yield values that are steady and physiologically significant. In general, this is accomplished by separately producing moving averages of the maximum and minimum peak values in such manner as to give greater weight to those peaks having amplitudes closer to the average amplitudes of their predecessors than to those having amplitudes that are significantly different from the amplitudes of their predecessors. Accordingly, a large positive peak that results from the detection of the amplitude of a single relatively large spike of noise will have very little, if any, effect on the average value that is displayed as the systolic pressure, and a large negative peak that results from the detection of the amplitude of a single relatively large spike of noise will have very little, if any, effect on the average value that is displayed as the diastolic pressure. In either case, the average values to be displayed will gradually change if there is a number of similar noise spikes occurring in succession. Thus, the displayed values can follow a step change in the signal level. On the other hand, if the amplitudes of the peaks gradually change, as during respiration cycles, the displayed values will be very close to the average of the peaks within the cycle. This is especially important in monitoring pulmonary artery pressures as the variation in the numerically displayed peaks is much reduced. In fact, it can be reduced to a value within the resolution of the display so that respiration has no effect.

THE DRAWINGS

FIG. 1 is a graphical representation of the output signals provided in accordance with this invention from data values that are hypothetically selected for purposes of illustration;

FIG. 2 includes a graph of an actual pulmonary artery pressure signal having a significant dwell between breaths as well as graphical representations of the values of systolic, mean, and diastolic pressures produced by apparatus constructed in accordance with the invention;

FIG. 3 includes a graph of an actual pulmonary artery pressure signal of a patient whose breathing is aided by a ventilator as well as graphical representations of the values of systolic, mean and diastolic pressures produced by apparatus constructed in accordance with the invention;

FIG. 4 includes a graph of an actual pulmonary artery pressure signal in which the respiratory pattern is such that neither systolic nor diastolic peaks have consistent amplitudes, as well as a graphical representation of the values of systolic, mean and diastolic pressures produced by apparatus constructed in accordance with this invention;

FIG. 5 includes a graph of an actual pulmonary artery pressure signal having spaced bursts of noise, as well as graphical representations of the systolic, mean and diastolic pressures produced by apparatus constructed in accordance with this invention;

FIG. 6 includes a graph of an actual pulmonary artery pressure signal having closely spaced bursts of noise, as well as graphical representations of the systolic, mean and diastolic pressures produced by apparatus constructed in accordance with this invention;

FIGS. 9A, 9B, 9C and 9D are flow charts for the program included in the specification that sets forth instructional steps by which a Hewlett-Packard 21MX series computer can be made to process data in accordance with the invention.

Figure 1:
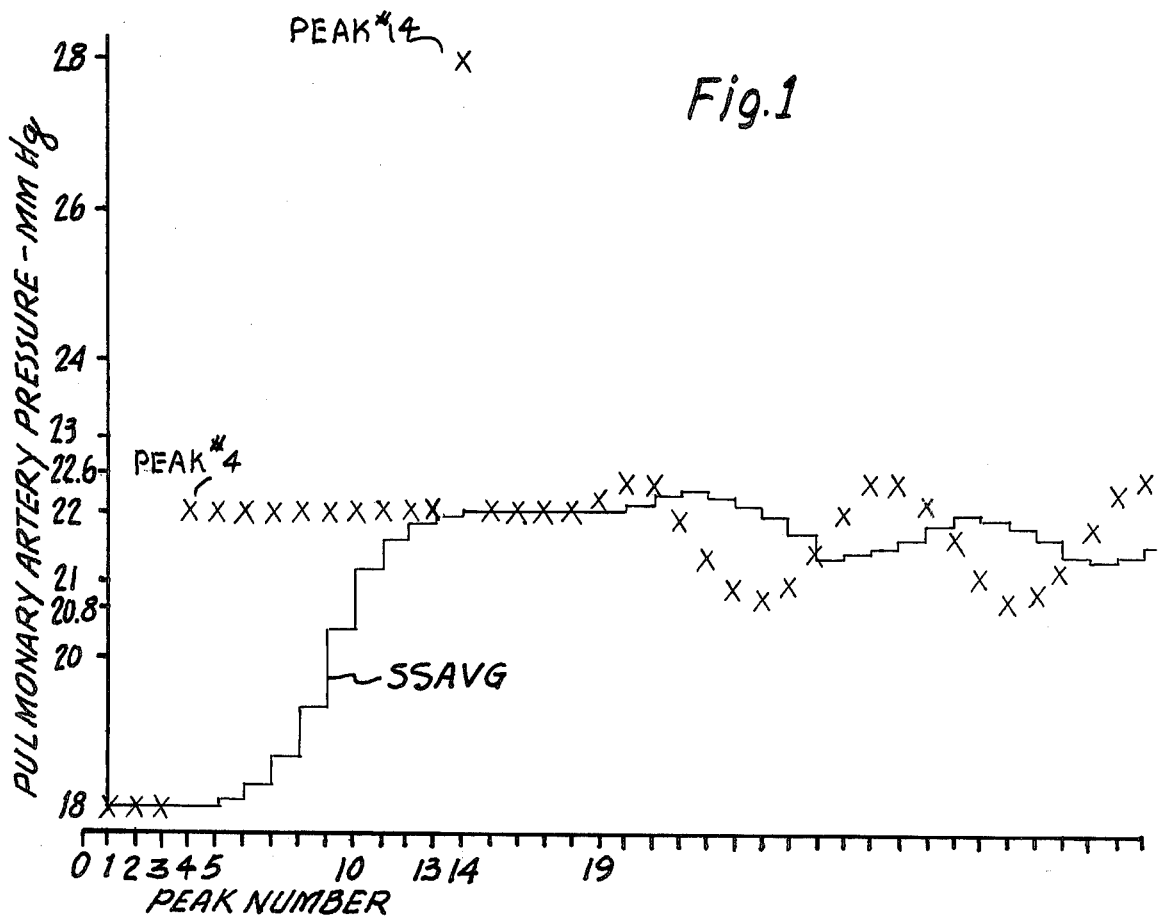

Before considering either analog or digital apparatus for processing a blood pressure signal in accordance with this invention, reference is made to the graphs of FIG. 1 for a brief discussion of the functions to be performed and an illustration of the advantage to be derived. In the drawing, the X's represent either maximum or minimum peaks of a pulmonary artery pressure and the solid line SSAVG represents a weighted average derived by apparatus constructed in accordance with this invention. Assume that the peaks have been at a constant amplitude long enough for the weighted average SSAVG to equal the constant amplitude of the first three peaks, and that the fourth peak has a significantly greater amplitude that is maintained through the peak number 13. The wave SSAVG increases in steps until it reaches the new amplitude. The height of successive steps increases until the one occurring at the time of the peak number 9 and then decreases. The increase is due to the fact that the differences between successive peaks 5 through 9 and an exponentially weighted average of the previous peaks are progressively less, so that the peaks are given greater weight in computing the height of the next step. The height of the steps at the peaks 10 through 13 gradually decreases because of limits that are arbitrarily selected to limit the amount of correction due to any change. Note in particular the peak number 14 that is at a much greater pressure than the peak number 13 and the fact that SSAVG changes very little in response to it. Thus, if this peak represented a large spike of noise, it would have very little effect on the value of SSAVG that is to be displayed. A similar result would be obtained if the single peak 14 were much less than the peak 13.

Starting with the peak number 19, it has been assumed for purpose of illustration that the peaks vary in a nearly sinusoidal fashion between the pressures of 20.8 and 22.6 mm Hg. Even larger variations would normally result from respiration. If the resolution of numerical display for the peaks is 1 mm Hg, it will vary from a reading of 20 to 22 mm Hg. Note, however, that the peak-to-peak amplitude of the wave SSAVG that is produced during the sinusoidally varying peaks is about one-third of the peak-to-peak amplitude of the peaks, so that the numerical indicator would remain at 22 mm Hg and not fluctuate. This represents the kind of reaction the invented apparatus has to undulating variations of low frequency that occur, for example, as a result of respiration. Actually, the constant variation in pressure due to respiration is larger than that shown, so that an indicator may exhibit changes in numerical value, but in any event they will be much smaller with the invention than without it.

FIGS. 2 through 6 show actual results obtained by the invention under various conditions. In all of these figures, the blood pressure signal is indicated by PDATA; the top horizontal line segments generally indicated by SP are the systolic pressures attained; the intermediate horizontal line segments generally indicated by MP are the mean pressures; and the lowest horizontal line segments generally indicated by DP are the diastolic pressures. It will be noted that any changes in level of the line segments occur at regular intervals, rather than after each peak as in FIG. 1. This result is obtained by sampling the averages at spaced intervals.

Figure 2:
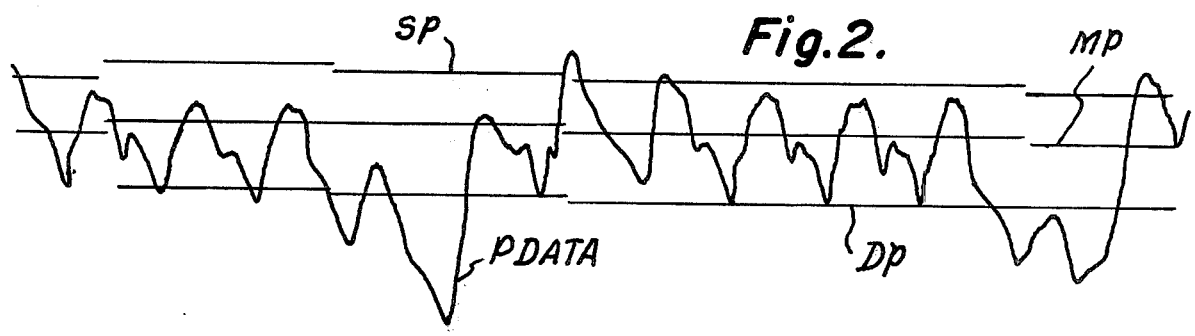
Figure 3:
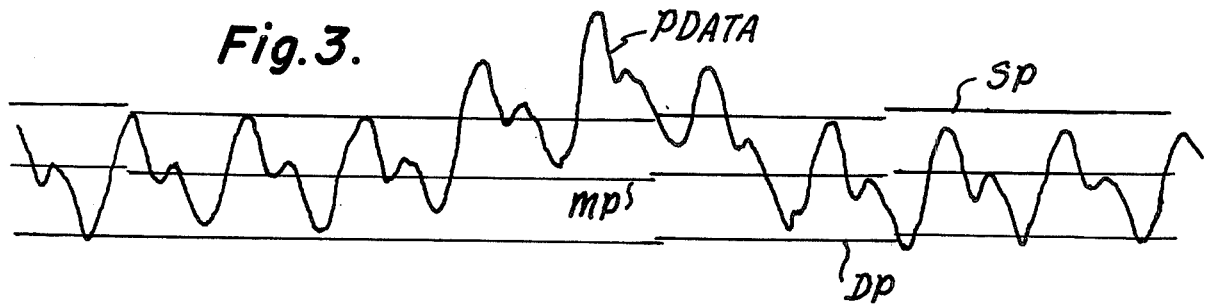

FIG. 2 illustrates a blood pressure signal PDATA in which there is a significant dwell between breaths during which both maximum and minimum peaks are sufficiently consistent to cause them to be entered into their respective averages with a strong weighting factor. The sporadic peaks on either side of this dwell depart from the average so as to have very little effect. As a result, the values of SP, MP and DP that are to be indicated by a numerical display vary only slightly. A similar result is attained in FIG. 3 that illustrates a blood pressure signal obtained from a patient on a ventilator.

Figure 4:
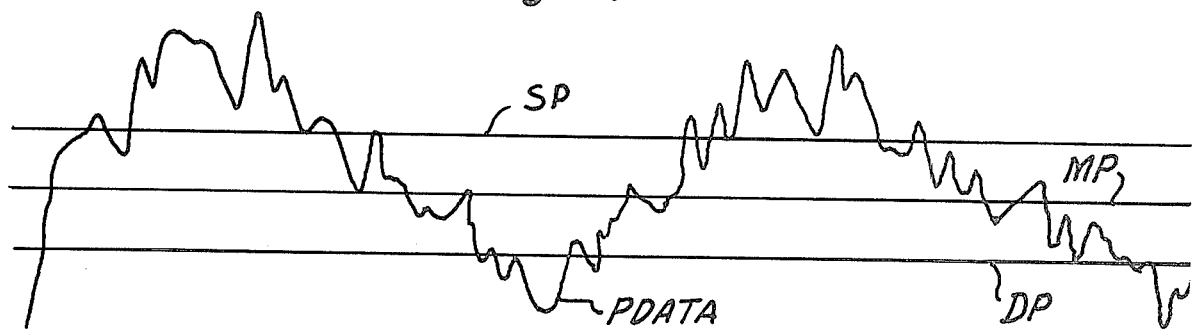

When, as in FIG. 4, the blood pressure signal PDATA exhibits a respiration pattern such that neither the systolic nor the diastolic peaks have consistent amplitudes, the pressure values of SP, MP and DP tend to be the averages of all the respective peaks.

Figure 5:
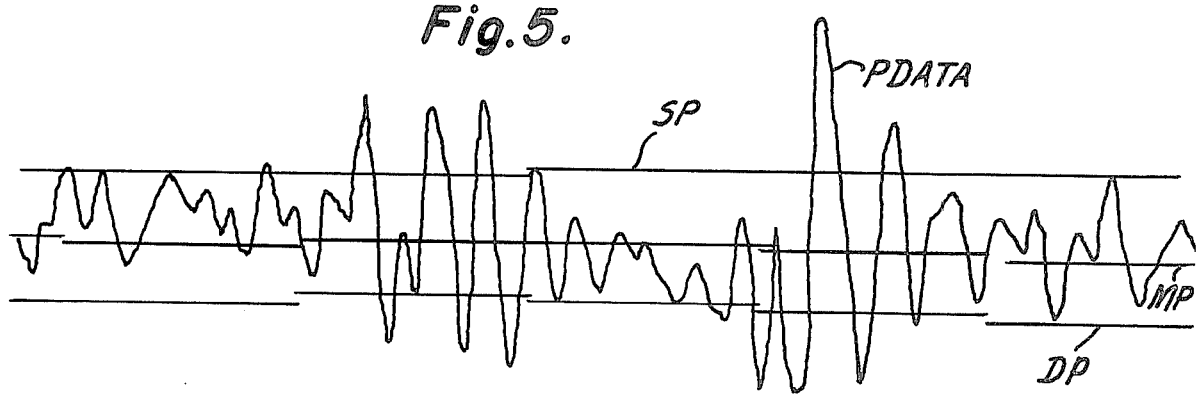
Figure 6:
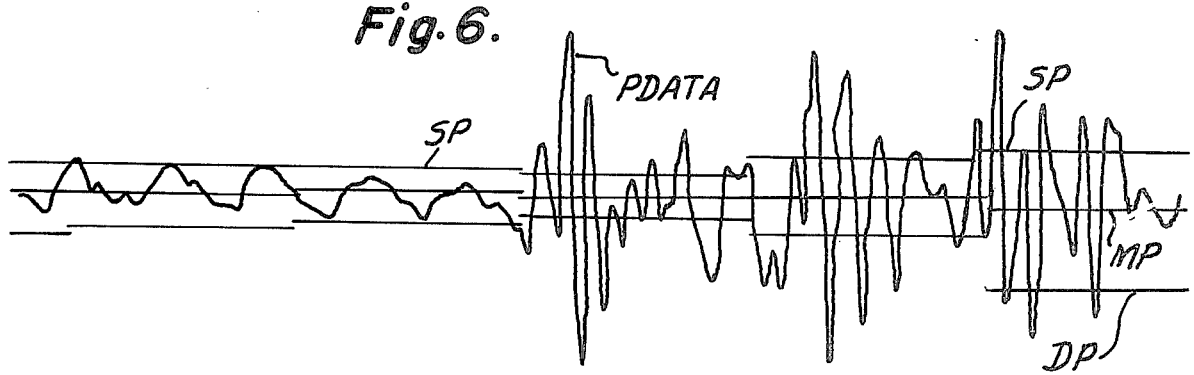

Intermittent bursts of noise, such as illustrated in FIG. 5, have little effect on the values of SP, MP and DP, but a rapid succession of bursts of noise, such as illustrated in FIG. 6, does have some effect on these values.

Figure 7A:
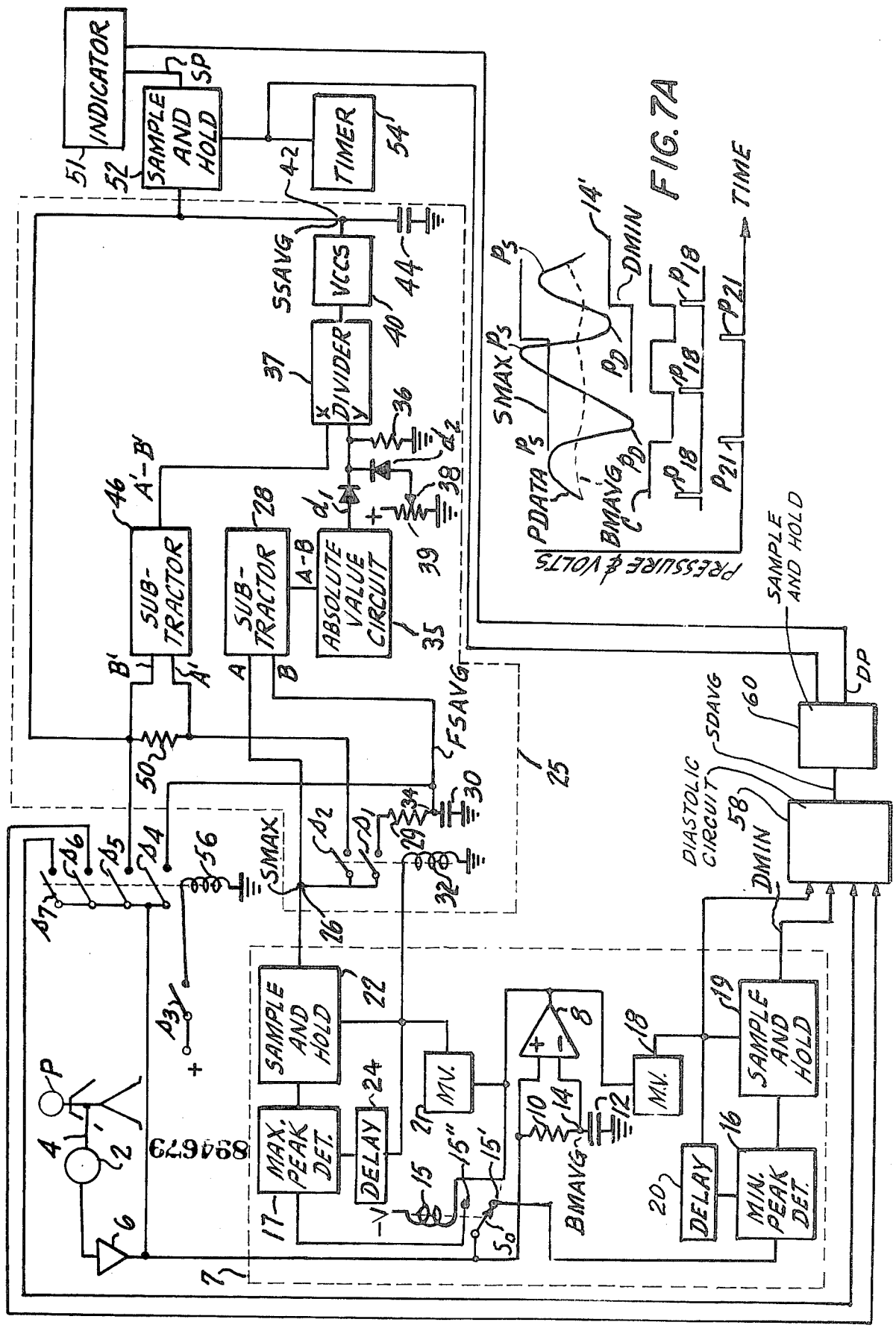
FIG. 7 is a diagram of the invented circuit and FIG. 7A includes graphs used in explaining FIG. 7.

FIG. 7 is an analog circuit for processing the signals in accordance with this invention. A blood pressure signal PDATA, such as illustrated in FIG. 7A, is derived from a patient P by coupling the blood pressure at an appropriate point in his circulatory system to a transducer 2 with a catheter 4. The output signal of the transducer 2 corresponds to the signal PDATA and is coupled via an amplifier 6 to means within the dotted rectangle 7 for deriving signals SMAX, each of which corresponds to the amplitude of the most recent maximum peak $P_S$ of the signal PDATA, as well as signals DMIN, each of which corresponds to the amplitude of the most recent minimum peak $P_D$. Various means may be used for this purpose, but the particular one illustrated is a simplified form of the system disclosed in my U.S. Patent Application, Ser. No. 895,193, filed on Apr. 10, 1978, and entitled "Beat-to-Beat Systolic and Diastolic Indicator". For reasons that will be explained, the means 7 also provides pulses respectively indicating when SMAX or DMIN have attained a value to be processed. These pulses could be provided by other means, such as a QRS detector operating upon the ECG signal.

The circuits within the dotted rectangle 7 may be described as follows. The signal PDATA at the output of the amplifier 6 is applied to the non-inverting input of a comparator 8 and to a low pass filter for deriving the approximate mean BMAVG of the signal PDATA. The filter is comprised of a resistor 10 and a capacitor 12 connected in series to ground. The signal BMAVG appears at their junction 14 and is coupled to the inverting input of the comparator 8. Whenever PDATA is greater than BMAVG, the output of the comparator 8 is high, and when PDATA is less than BMAVG, the output of the comparator 8 is low, as indicated by the waveform C of FIG. 7A. The output of the comparator 8 is connected to one end of a relay coil 15, the other end being connected to a low voltage $-V$. When the output of the comparator 8 is high, the coil 15 is energized so as to pull a switch $s_0$ from the normal position shown, where it contacts a terminal 15' that is connected to the input of a minimum peak detector 16, to a position where it contacts a terminal 15" that is connected to the input of a maximum peak detector 17. The switch $s_0$ is connected to the output of the amplifier 6 so that it applies the signal PDATA to one peak detector or the other.

The output of the comparator 8 is connected to a positive edge triggered single-shot multivibrator 18 that produces pulses $P_{18}$ whenever PDATA crosses BMAVG in an upward direction. These pulses are applied to set a sample-and-hold circuit 19 and via a delay 20 to clear the minimum peak detector 16. Thus, the signals DMIN of FIG. 2A appear at the output of the sample-and-hold circuit 19.

The output of the comparator 8 is also connected to a negative edge triggered one-shot multivibrator 21 that produces pulses $P_{21}$ whenever PDATA crosses BMAVG in a downward direction. These pulses are applied to set a sample-and-hold circuit 22 and via a delay 24 to clear the maximum peak detector 17. Thus, the signals SMAX of FIG. 2A appear at the output of the sample-and-hold circuit 22.

Processing of a maximum peak signal SMAX is accomplished by the circuits within a dotted line 25 in the following way. The signal SMAX at the output of the sample-and-hold circuit 22 is coupled to an input terminal 26 that, in turn, is connected to the A input of a subtractor 28. The terminal 26 is also connected to means for deriving a voltage FSAVG, fast systolic average, equal to an average of the most recent values of SMAX. In this particular circuit, the means is comprised of a normally open switch $s_1$ connected between the input terminal 26 and a low pass filter comprised of a series combination of a resistor 29 and a capacitor 30. The pulses $P_{21}$ at the output of the multivibrator 21 are applied to a relay coil 32 that operates the switch $s_1$. When it closes, it effectively samples SMAX and applies the sample to the filter. The values of the resistor 29 and capacitor 30 in combination with the duration of the pulse $P_{21}$ determine the speed with which the voltage FSAVG at the junction 34 of the capacitor 30 and the resistor 29 follows the changes in the amplitudes of the signal SMAX. Values chosen so as to make the change in voltage equal half the voltage across the resistor 29 at the beginning of each pulse have been found to work well, but other values can be used. In any case, the value of FSAVG is the average of very recent values of SMAX. The voltage FSAVG at the junction 34 is applied to the B input of the subtractor 28. The effecto of each sample of SMAX on the voltage across the capacitor 30 decreases exponentially with the number of succeeding samples, so that theoretically the voltage on the capacitor 30 is the result of all samples that have occurred since the apparatus was turned on, but the most recent sample has the greatest effect, and the effect of each successive previous sample is less.

The output of the subtractor 28 is A-B and therefore equal to the value of SMAX minus the value of FSAVG, which is the difference between the amplitude of the current value of SMAX and the average of the amplitudes of a few recent values of SMAX. Whether the output of the subtractor 28 is positive or negative, it is made to be a positive voltage of the same numerical value by an absolute value circuit 35. The output of the absolute value circuit 35 is a divisor control voltage and is applied via a diode $d_1$ to a divisor input Y of a divider 37. A resistor 36 is connected between the Y input and ground. In order to provide a minimum value of positive voltage at the divisor input Y, a diode $d_2$ is connected between a tap 38 on a potentiometer resistor 39 and the divisor input Y. The resistor 39 is connected between a point of positive voltage and ground.

The manner in which the voltage applied to the dividend input X of the divider 37 is derived will be explained at a later point. The output of the divider 37, X/Y, is applied via a voltage controlled current source 40 to an output terminal 42 so as to charge or discharge an output capacitor 44 that is connected between the terminal 42 and ground by an amount proportional to X/Y. The voltage of the terminal 42, SSAVG, is the weighted moving average of the values of SMAX that is to be used for display purposes.

The voltage at the dividend input X of the divider 37 is derived as follows. A connection is made between the output terminal 42 and an input B' of a subtractor 46. A normally open switch $s_2$ that is operated by the relay coil 32 is connected between the input terminal 26 and the other input A' of the subtractor 46. A resistor 50 is connected between the inputs A' and B'. In between pulses $P_{21}$, when the relay coil 32 is not energized and the switch $s_2$ is open, the voltage SSAVG at the output terminal 42 is applied to both inputs A' and B' of the subtractor 46, so that its output is zero. During the pulses $P_{21}$, the switch $s_2$ is closed so as to apply the current value of SMAX at the input terminal 26 to the A' input of the subtractor 46. Its output A'-B' during the pulses $P_{21}$ is therefore equal to the difference between the current maximum SMAX and the old value of the moving average SSAVG. This output is applied to the dividend input X of the divider 37.

Thus, if a maximum detected peak of PDATA abruptly increases to a much larger value so that a much larger value of SMAX appears at the input terminal 26, the difference between this value of SMAX and the moving average SSAVG is divided by an amount proportional to the difference between the value SMAX and the average amplitude of a small number of previous peaks determined by the time constant of the resistor 29 and the capacitor 30 and the duration of the pulses $P_{21}$. In certain cases, this is necessarily modified by the application of the minimum positive voltage to the input Y of the divider 37 in order to prevent the divisor from being zero.

Referring again to FIG. 1, assume that the Xs indicate values of data peaks having corresponding values of SMAX. As SSAVG gradually approaches the level of peaks 4 through 9, A-B, or SMAX-FSAVG, gets smaller so that the amount of charge placed on the output capacitor 44 during successive pulses $P_{21}$ increases. From peak 10 through peak 13, the increase becomes less because the dividend A'-B', or SMAX-SSAVG, gets smaller and the divisor is limited to the value set by potentiometer 39. It can be seen that the moving average SSAVG does not change in response to the much larger peak number 4 because, even though SMAX-SSAVG is large, the value of A-B, or SMAX-FSAVG, that determines the magnitude of the divisor is also large.

Even though the value of the moving average SSAVG at the output terminal 42 can change at the time of the pulses $P_{21}$, the changes to be applied to an indicator 51 can be made to occur at a slower rate by coupling it via a sample-and-hold circuit 52 to the output terminal 42 and triggering it at suitable times with pulses from a timer 54. This accounts for the fact that changes in the amplitudes of the horizontal line segments SP, MP and DP of FIGS. 2 through 6 occur less frequently than the peaks in the signal PDATA.

Initialization

In order to initialize the circuit, power is applied by means not shown, and a switch $s_3$ is momentarily closed so as to energize a relay coil 56 and close normally open switches $s_4$, $s_5$, $s_6$ and $s_7$. The closure of the switch $s_4$ applies the PDATA signal from the amplifier 6 to the capacitor 30; the closure of the switch $s_5$ applies the PDATA signal to the output capacitor 44; and the closure of the switches $s_6$ and $s_7$ applies the PDATA signal to the same points in a circuit not shown but contained within a rectangle 58 for deriving the current value of the diastolic pressure in the same manner as the systolic voltage is derived. The pulses $P_{18}$ from the multivibrator 18 and the voltage DMIN at the output of the sample-and-hold circuit 19 are also applied to the circuit 58. The diastolic circuit contained in the rectangle 58 is assumed to be the same as those portions of the systolic circuit contained within the dotted enclosure line 25. Its output may be applied to the indicator 51 via a sample-and-hold circuit 60 that is triggered by pulses from the timer 54.

Operation

From the description above, it can be seen that a new current value of SSAVG is developed across the output capacitor 44 in response to each of the pulses $P_{21}$. The amount by which it is changed depends on the output of the divider 37. This output is equal to the value of the voltage applied to its dividend input X, which is equal to the difference between the value of the current systolic peak SMAX and the old value of SSAVG divided by the greater of the voltages at the tap 38 or the absolute value of SMAX-FSAVG. Thus, $$SSAVG \text{ (new)} = SSAVG \text{ (old)} + \frac{SMAX - SSAVG \text{ (old)}}{F} \quad (1)$$

The potentiometer 39 and its tap 38 insure that F will never be below some given value.

The value of F is proportional to the absolute value of the difference between the amplitude of the current systolic peak SMAX and the former systolic average FSAVG that is derived by the subtractor 28. Therefore, we can say $$F = \left| \frac{SMAX - FSAVG}{K} \right| \quad (2)$$

where K is determined by the gains of the subtractor 28 and the absolute value circuit 35. The value of F is held to a minimum by the potentiometer 39 so as to limit the change in value of SSAVG for each beat. This also avoids dividing by zero. Substituting, $$SSAVG \text{ (new)} = SSAVG \text{ (old)} + K \frac{|SMAX - SSAVG \text{ (old)}|}{|SMAX - FSAVG|}$$

where the minimum value of the denominator SMAX-FSAVG is established by the setting of the tap 39 on the potentiometer resistor 38.

Expressing these values in millimeters of mercury, appropriate values have been determined to be:

|  | K | \|SMAX-FSAVG\| minimum |
|---|---|---|
| Radial Artery Pressure | ½ | 1 |
| Pulmonary Artery Pressure | 1/10 | 1/5 |

During the time that $s_2$ is closed, the output of the subtractor 46 can be seen to represent an "error signal" or the disagreement between the signals at the input terminal 26 and the output terminal 42. When $s_2$ is opened, the signal SSAVG is applied by the resistor 50 to the A and B inputs of the subtractor 46 so as to cause the error signal to be zero. The value of F, $$\left| \frac{SMAX - FSAVG}{K} \right|,$$

is seen to control the amount of adjustment that the "error signal" is allowed to make to the signal at the output terminal 42, i.e., to the voltage across the capacitor 44.

Stated in a general way, it can be said that the subtractor 46 is a means for providing a difference signal representing the difference between the current value of SMAX and the old value of the moving average SSAVG that may be used in producing a numerical display, and that the subtractor 28 is a means for providing a signal indicative of the portion of the difference signal that is to be used in changing the old value of the moving average SSAVG to a new value.

The means within the dotted rectangle 7 provides signals SMAX and DMIN as well as pulses $P_{18}$ and $P_{21}$ that respectively indicate when new values of SMAX and DMIN have been respectively determined, i.e., a pulse $P_{18}$ occurs just after the search for the value DMIN of a diastolic peak $P_D$ has been completed and a pulse $P_{21}$ occurs just after the search for the value SMAX of a systolic peak $P_S$ has been completed. The values of DMIN and SMAX at the outputs of the sample-and-hold circuits 19 and 22 correspond to the amplitudes of these peaks. By effectively sampling SMAX and DMIN with the pulses $P_{21}$ and $P_{18}$, the voltage FSAVG on the capacitor 30 is unaffected by the spacing between peaks. If the spacing is constant and known, the pulses could be dispensed with and the low pass filter comprised of the resistor 29 and the capacitor 30 could be connected directly to the terminal 26 and could be made to have a time constant such as to provide the same value of FSAVG. The time constant could be varied as the spacing varied. Whereas peaks due to systolic and diastolic pressures may have a fairly consistent spacing, it can be seen from FIGS. 5 and 6 that noise peaks do not, so that the use of a filter alone would provide values of FSAVG that are dependent on spacing rather than on amplitude alone. For this reason, it is preferable that some means be provided for sampling new values of SMAX and DMIN. The diastolic peaks are processed in an identical fashion by means not shown within the rectangle 58.

Comment

In the circuit of FIG. 7, the pulses $P_{21}$ are applied to the relay coil 32 so as to close the switch $s_1$ during each pulse, thereby obtaining a sample of each new value of the analog stepped signal SMAX. During the same time, the switch $s_2$ is closed so that the subtractor 46 can derive the difference between the sample and the former value of SSAVG at the output terminal 42. Operation in this manner relates the average SSAVG to prior samples of SMAX regardless of how far apart they may be. If it is desired to relate SSAVG to the time average of SMAX, the switches $s_1$ and $s_2$ could remain permanently closed and the relay 32 could be dispensed with, along with pulses applied thereto.

In either case, one can consider that the low pass filter comprised of the resistor 29 and the capacitor 30, the subtractor 28 and the absolute value circuit 35 is a differentiating means for determining the absolute value of the slope of a signal; that the divider 37, the VCCS circuit 40 and the capacitor 44 effectively constitute a low pass filter having a variable time constant determined by the differentiating means; and that the subtractor 46 is a means for determining the difference between the current value of the signal and the output of the low pass filter just described. Thus, when the absolute value of the slope of the signal is large, as in the case of sample numbers 3 and 14 of FIG. 1, the effective time constant of the low pass filter is made large so that the output of the filter is changed very little and, conversely, when the slope of the signal is low, as in the case of samples 4 through 13 of FIG. 1, the effective time constant of the low pass filter is small so that the output of the filter is changed by a greater amount.

In the case considered, the signal that is processed is the variation of the maximum peaks or SMAX rather than the entire blood pressure signal PDATA, but the circuit could be used to continuously process a signal that is expected to have slopes within a given range so as to reduce the effect of portions of the signal having slopes that are outside that range.

Description of a Digital Signal Processor

Direct processing of the blood pressure signal PDATA at the output of the amplifier 6 of FIG. 7 so as to derive maximum and minimum peaks and the production of stable values thereof in accordance with this invention can be carried out by digital logic circuits as well as by the analog circuits of FIG. 7. Circuits operating in this manner are described in connection with the Hewlett-Packard 21MX series computer, but it will be apparent to those skilled in the art that other computers could be used. It is contemplated that the computer will be an integral part of the monitoring equipment of which this invention forms a part.

Figure 8:
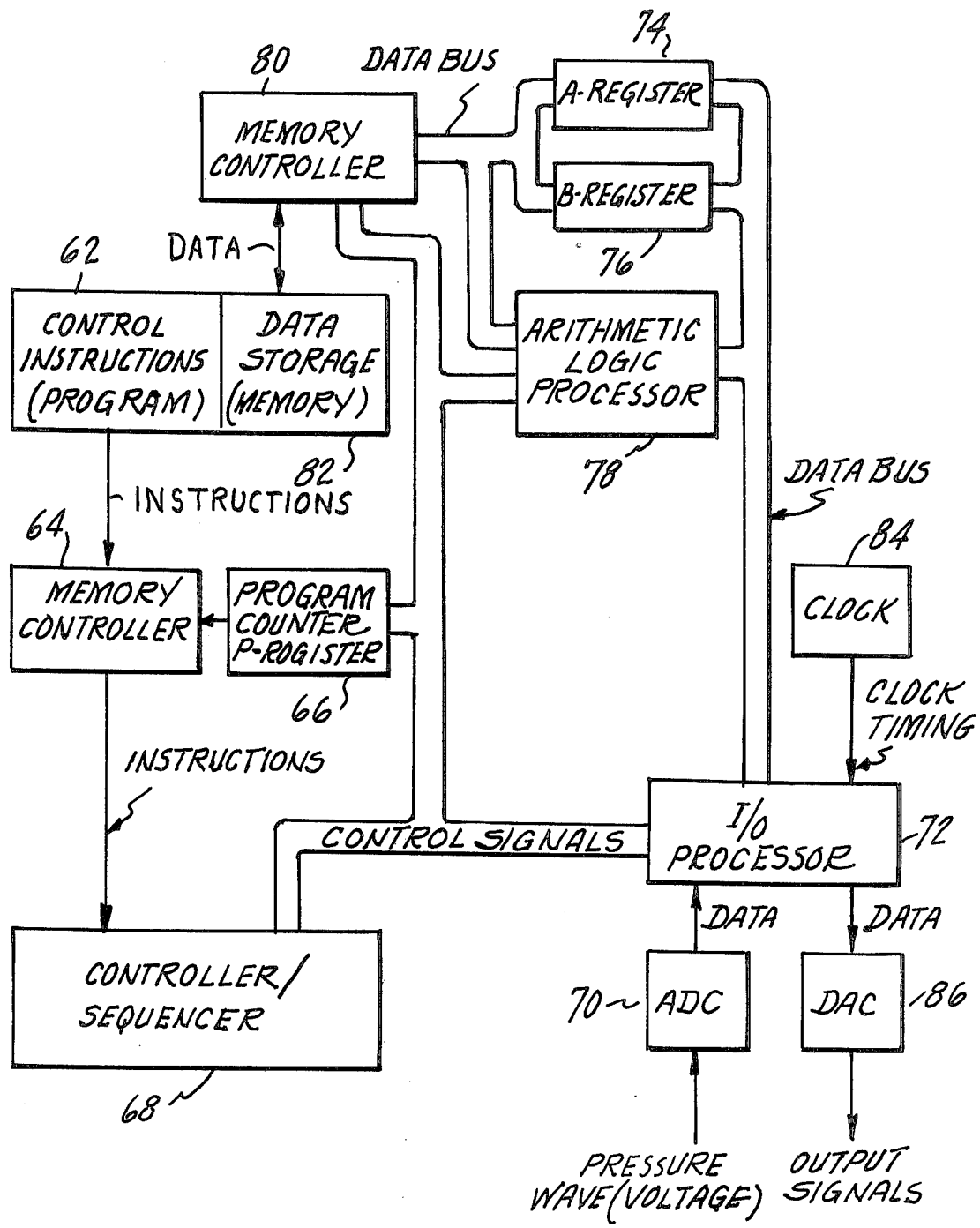
FIG. 8 is a block diagram of the functional parts of a digital circuit for processing data in accordance with the invention.

FIG. 8 is a block diagram of functional digital units required for carrying out the invention. Control of the flow of data as well as the operations performed on the data are determined by instructions stored at different locations in a ROM or instruction memory 62. Instructions are fetched from the memory 62 by a memory controller 64 in response to commands from a program counter or P register 66 and applied to a controller/sequencer 68.

The analog blood pressure signal PDATA at the output of the amplifier 6 of FIG. 7 is converted into its digital form by an analog-to-digital converter 70 and applied to an input of an input/output processor 72. The converter 70 samples the analog wave PDATA at intervals determined by a clocking device 84, which is distinct from the computer clock, not shown, contained in the controller/sequencer 68. The sequencer controls the application of the digitized PDATA to an A register accumulator 74 and a B register accumulator 76 that are part of an arithmetic processor including an arithmetic logic processor 78, and it also may cause a memory controller 80 to take data from one of the accumulators 74 or 76 or the logic processor 78 and place it into a read/write data storage memory 82 or vice-versa. The data storage memory 82 may share the same physical memory with the control instruction memory 62 and both memories may be controlled by the same memory controller, but separate memories and controllers are shown so as to more clearly identify the roles played by each.

All operations involving data manipulation usually take place in the accumulators 74 or 76. A program instruction may, for example, cause the controller/sequencer 68 to request the arithmetic logic processor 78 to perform some operation involving one or both of the accumulators. Whether the operation includes adding, dividing, negating, multiplying, shifting, rotating, Boolean manipulation (AND, OR), or testing, the results stay in an accumulator. If the value in the accumulator is to be stored in the data memory 82, a separate instruction will be given to the memory controller 80 by the controller/sequencer 68.

Instructions may be taken from the control instruction memory 62 by the memory controller 64 with a sequence other than normal by resetting the program counter 66 with the arithmetic logic processor 78 or with the controller/sequencer 68, e.g., a test compare instruction could result in the contents of the program counter or P register 66 being modified so as to cause it to select an alternate branch in the stream of program instructions derived from the control instruction memory 62.

An external clock 84 provides asynchronous timing pulses to the input/output processor 72 causing it to inform the controller/sequencer 68. This results in the program counter 66 being shifted to a timing section of the program that might, for example, request the input/output processor 72 to sample the analog blood pressure signal PDATA with the A-D converter 70 and place it in the data memory 82 via one of the accumulators 74 or 76. After the timing section of the program is completed, the program counter 66 is set back to allow the computer to resume its normal processing.

When all manipulations of data have been completed so as to derive digital signals respectively representative of stable values of maximum or minimum peaks of the blood pressure signal PDATA, the controller/sequencer 68 issues a command signal causing the input/output processor 72 to apply the digital signal to a digital-to-analog converter 86 that converts it to an analog signal corresponding to the peak in question.

Operation of the Digital Processor in Accordance with the Invention

The manner in which a Hewlett-Packard 21MX series computer processes signals representing samples of data so as to provide a moving average in which the contribution of each sample is weighted in a generally inverse relationship with respect to the deviation of its amplitude from an average of the amplitudes of a few previous samples will now be explained by reference to the flow charts of FIGS. 9A, 9B, 9C and 9D. A step in the program set forth at the end of the specification that is pertinent to each block in the flow charts is set forth in nearby parentheses. Steps in the program indicated by an asterisk (*) are not actual computer steps, but are included for the purpose of explanation. Reference will be made where appropriate to circuit components of FIG. 7 and to the block diagram of the computer shown in FIG. 8, but identification of the figures referred to is not thought to be required in each case. It should be kept in mind that FIG. 7 only shows the details of the portion of the analog circuit that derives the systolic moving average SSAVG, whereas the program includes steps for deriving both systolic, diastolic, and mean moving averages SSAVG and SDAVG. Statements to the effect that certain functions are done by or in a block means that they are done by the relevant portion of the program and not actually by the block per se.

Initialization

Figure 9A:
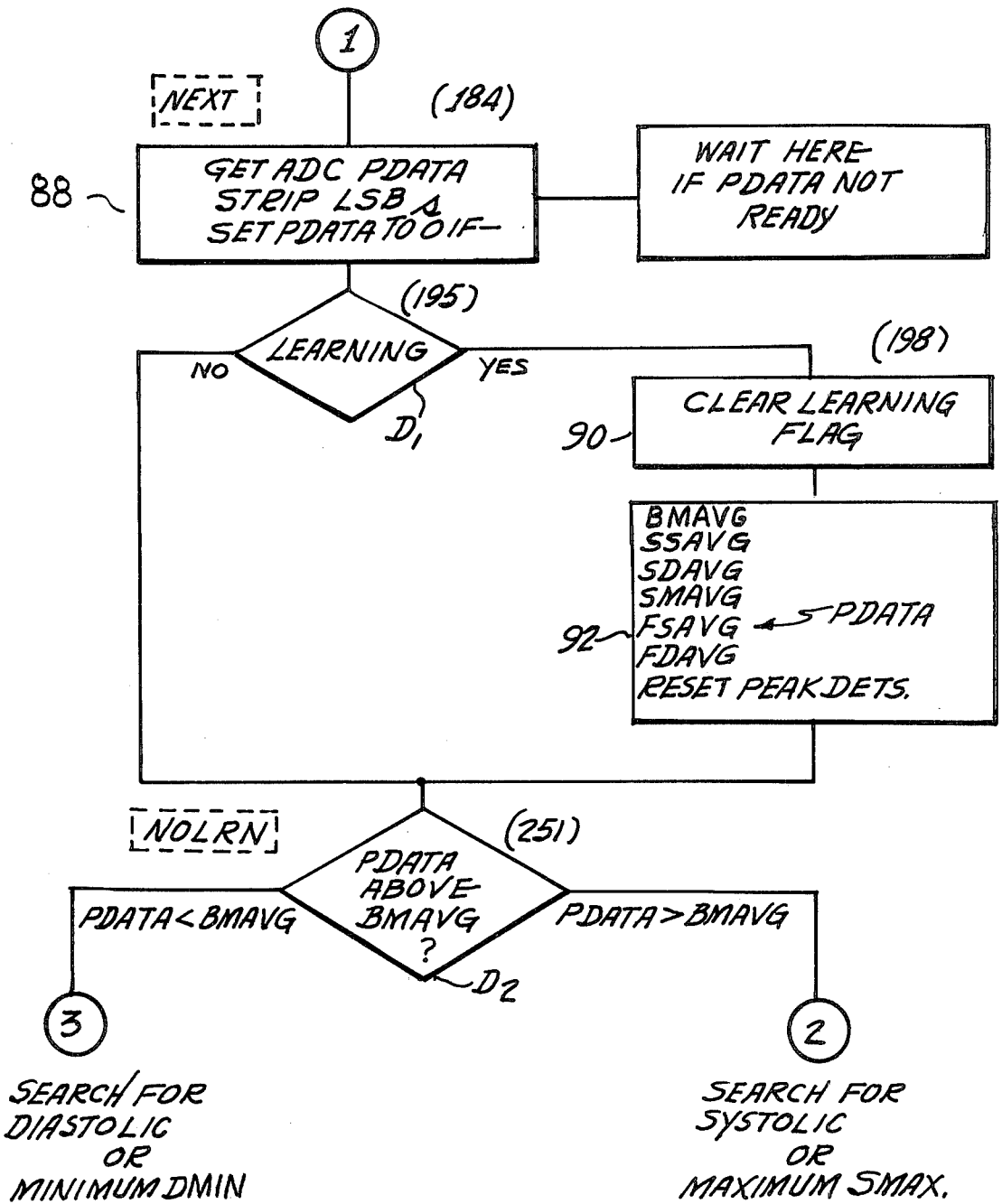

The digital form of the blood pressure signal PDATA at the output of the analog-to-digital converter 70 of FIG. 8 is transferred into the accumulator 74 as indicated in the block 88 of FIG. 9A. As only twelve significant bits are handled by the converter 70, the least significant four bits are set to zero because their values are not known. Negative blood pressures are not encountered, so that if PDATA is negative, it must be due to an artifact. Therefore, if PDATA is negative, its value is arbitrarily set to zero.

If the equipment has just been turned on, as is done in the circuit by closing the switch $s_3$, this fact is detected by a test block $D_1$. In this event, the learning flag is cleared in block 90, which corresponds to opening the switch $s_3$. The equipment is then initialized by carrying out the functions indicated in block 92. The outputs where the average SSAVG of the maximum peaks and the average SDAVG of the minimum peaks appear are set to the value of PDATA, a function performed in the circuit of FIG. 7 by the closure of the switches $s_5$ and $s_6$. In the program, the mean pressure SMAVG is also set to the value of PDATA, but the derivation of the mean is not shown in the circuit. The peak detectors are reset, a function performed in the circuit by the pulses from the multivibrators 18 and 24, and finally, the values of FSAVG and FDAVG are set at the value $P_O$ of PDATA at the time $t_O$. In the circuit, this latter function is done by closure of the switches $s_4$ and $s_7$. BMAVG is set to PDATA, but this is not shown in the circuit of FIG. 7 because it is not necessary.

After initialization, or if the answer by the decision block $D_1$ is to the effect that initialization is not required, a decision block $D_2$ determines whether PDATA is above or below the reference, which in this case is BMAVG. If the preferred system of my above-identified patent application is used, the reference will be BMAVG plus or minus offsets that are used to reduce the false peaks caused by certain undesired perturbations which may be present in the signal PDATA. If the answer of the decision block $D_2$ is the PDATA is higher than BMAVG, go to point ② in FIG. 9B; but if it is lower, go to point ③ in FIG. 9C.

Systolic Processing and Search for Minimum Value of DMIN

If $D_2$ indicates that PDATA is below the reference BMAVG, a decision block $D_3$ in FIG. 9B tests whether this is the first sample below BMAVG. This is done by noting whether the value of DMIN is the unique value, +32767, that is inserted in the memory 82 during initialization by the block 92 or by a block 100' of FIG. 9C during normal operation. In the circuit, the first value of PDATA below BMAVG is identified by a pulse $P_{21}$ provided by the negative edge triggered one-shot multivibrator 21. When $D_3$ indicates that a first sample of PDATA below BMAVG has been received, the following functions are performed.

As indicated in block 94, the unique value of DMIN in the data storage memory 82 is changed to PDATA. Succeeding samples of PDATA will therefore cause the block $D_3$ to give a negative answer rather than a positive answer. A negative answer causes a decision block $D_4$ and a block 96 to search for a minimum value of DMIN, just as the detector 16 in the circuit. $D_4$ tests each sample of PDATA to determine if it represents a pressure less than the last value of DMIN. If it is not less, DMIN remains the same, but if it is less, the block 96 updates DMIN in the memory 82. In either case, proceeed to point ④ in the flow charts or GMEAN in the program, at which a new value of BMAVG is calculated, as will be explained in connection with FIG. 9D.

An answer in $D_3$ indicating that a first sample of PDATA has been received that is below the threshold also causes the functions indicated in blocks 98 and 100 to be performed so as to derive the weighted averages SSAVG and SMAVG that are desired. In the program, a more slowly changing mean of PDATA, termed SMAVG, is derived, although this is not represented in the circuit.

In block 98, the smoothness factor F of PDATA is calculated by substracting the old value of FSAVG from the current value of SMAX and dividing by a constant K. This is done in the circuit by a subtractor 28 and the absolute value circuit 35. The division by a constant K, which is shown to be 16 in the block 98, is accomplished by the internal gains of the subtractor 28 and the absolute value circuit 35. The minimum value of F is established by the voltage supplied to the Y input of the divider 37 via the diode $d_2$.

Derivation of a new value of FSAVG is done by adding the current value of SMAX to the old value of FSAVG and dividing by a constant indicated as being 2. This function is performed by the filter 29, 30 and the closure of $s_1$.

The desired weighted average of the values of SMAX is calculated by subtracting the old value of SSAVG from the present value of SMAX, dividing by F, and adding the result to the old value of SSAVG. In the circuit, the difference SMAX-SSAVG is derived by the subtractor 46 and the division by F is done in the divider 37. The addition of the results of this division to the old value of SSAVG is done by charging or discharging the capacitor 44. As explained, the value of SMAVG calculated in the block 98 is not performed in the circuit, but represents an averaging of the signal BMAVG with a time constant one-half that used for SSAVG. BMAVG is also updated by a similar process in the diastolic circuit 58, or as described in FIG. 9C. Since it is updated twice as frequently as either SSAVG or SDAVG, it will have a net time constant of update which is comparable to both.

Diastolic Processing and Search for Maximum Value of SMAX

If the test in decision block $D_2$ of FIG. 9A indicates that PDATA is above the threshold, the functions indicated in FIG. 9C are performed, but because they are the same, except for the values used, the blocks in FIG. 9C corresponding to the blocks in FIG. 9B have the same designations, primed. The values used are indicated within the blocks. The step numbers in the program are different. These functions are carried out by diastolic circuits that are assumed to be within the rectangle 58, but not shown.

Updating BMAVG

In FIG. 9D, a new value of BMAVG is continuously calculated by dividing the difference between PDATA and the old value of BMAVG by a constant, which in the particular example is 16. The result is then added to the old value of BMAVG. In the circuit, this function is performed by the low pass filter comprised of the resistor 10 and the capacitor 12.

Example Calculation

That the hardware of the computer is controlled in a manner that is fully equivalent to the operation of the hardware represented in the schematic diagram of FIG. 7 will now be illustrated by an example. Reference will be made to the block diagram of the computer illustrated in FIG. 8, when appropriate.

Let us consider the resistor 10 and capacitor 12 that filter the input value PDATA to derive its approximate mean BMAVG. The equivalent function is performed by the computer program steps 809 through 819 that occur at the label GMEAN in the program and on the flow chart in FIG. 9D. The mathematical basis of this computation is described in lines 800 to 807 of the program. It may be shown that if this computation is performed at a regular interval, with a value of PDATA representing the input to the RC filter 10, 12, that the value BMAVG derived by the computer will behave identically as a function of time to the voltage BMAVG on the capacitor 12.

This computation is implemented in the computer as follows. The instruction on line 809 causes the memory controller 80 to retrieve the numeric value representing BMAVG from the data storage memory 82 and enter this value into the A register 74. The next instruction on line 810 causes the contents of the A register 74 to be negated. The instruction on line 811 causes the value PDATA to be retrived from the data memory 82 and added to the contents of the A register 74, the result, PDATA-BMAVG, remaining in that register. The instructions on lines 812 and 813 cause the contents of the A register to be shifted to the right four places. This results in the binary value, PDATA-BMAVG, being divided by 16. This operation is performed by the arithmetic and logic processor 78 of the computer and the results remain in the A register. The next two instructions are provided to prevent deadband when the divisor has a value lying between 0 and 15, and is therefore not represented in the RC equivalent. In line 818, the instruction causes the value BMAVG to be fetched from memory 82 by the memory controller 80 and added to the A register accumulator. The last instruction causes the contents of the A register to be stored back into memory 82, replacing and updating the original value of BMAVG.

This process takes place for each new sample of PDATA which is acquired by the analog-to-digital converter at an arbitrary rate. A rate of 50 samples per second has been found to be suitable.

Program To Be Used with a Hewlett-Packard 21MX Series Computer

```
0155        HED              PROCESS NEXT DATA VALUE
0156    *
0157    *
0158    *    GET NEXT DATA POINT FROM PRESSURE BUFFER
0159    *
0160    *
0161  NEXT  LDX PPRC#
0162    *
0173        LDA 8,I          GET DATA
0174    *
0175    *    INSERT OVERRUN TEST HERE   ( IF NEEDED )
0176    *
0177        ISZ OUTPT
0178        NOP              BUMP RETRIEVAL COUNT
0179    *
0180    *
0181        AND =B177760     STRIP 4 LSB'S
0182        SSA
0183        CLA              DON'T ALLOW NEGATIVE
0184        STA PDATA
0185    *
0186    *
0187    *    CHECK FOR LEARNING BIT SET
0188    *        IF SET USE CURRENT DATA FOR STATUS DISPLAY
0189    *        STARTING VALUES.
0190    *
0191    *
0192        LDA LEARN
0193        CLF 0
0194        AND PCTPT,I      PCH
0195        SZA,RSS
0196        JMP NOLRN
0197    *
0198        CMA
0199        AND PCTPT,I      CLEAR LEARNING BIT
0200        STA PCTPT,I
0201        STF 0
0202    *
0203        LDA PDATA
0204        STA SDAVG
0205        STA SMAVG
0206        STA SSAVG
```

```
0235          LDA MINW
0236          STA SMAX        SET TO ENSURE
0237          LDA MAXW          THAT A BEAT
0238          STA DMIN            WILL BE FOUND NEXT TIME
0239 *
0240          LDA PDATA       CURRENT VALUE
0241          STA BMAVG       SET STATUS VALUES
0242          STA FDAVG
0243          STA FSAVG
0244 *
0245 *
0246          SKP
0247 *                        SYSTOLIC OR DIASTOLIC SEARCH?
0248 NOLRN CLB
0249 S/D?     LDA PDATA
0250          ADB BMAVG
0251          JSB CMPAB         A CONTAINS PDATA
0252          JMP SYSTS       ABOVE THRESHOLD
0253          JMP DIASS       BELOW TH     A<B
0254 *                         TH IS BMAVG
0255          NEG             SEARCH FOR NEXT SYSTOLIC VALUE
0256          SPC 2
0257 *                        NEW DATA VALUE IS IN "A" REG (PDATA)
0258 *
0259 SYSTS LDB SMAX           PREVIOUS MAX
0260       CPB MINW
0261       JMP FTSYS          FIRST TIME IN!
0262 *
0263          JSB CMPAB           NEW MAX ?
0264 *
0265          STA SMAX        NEW MAX
0266          JMP GMEAN
0267          NEG                     PROCESSING OF NEW DIASTOLIC VALUES
0268 *    FIRST TIME ON SYSTOLIC SIDE OF FENCE
0269 *    CALL THIS THE START OF A NEW BEAT
0270 *
0271 *
0272 FTSYS EQU *              FIRST TIME SYSTOLIC
0273 *
0274 *    SET SYSTOLIC TO CURRENT VALUE
0275          STA SMAX
0276 *
0281 *
0282 *    EVALUATE SMOOTHNESS OF CURRENT BEAT COMPARED TO FAST AVG.
0283 *
0284          LDB FDAVG       DIAS AVG
0285          CMB,INB
0286          ADB DMIN        DIAST-FAST AVG
0287 *
0288          SSB             ABS VALUE
0289          CMB,INB
0290 *
0291 *    SCALE SMOOTHNESS (NOT LESS THAN 2)
0292 *
0293          LSR 4           DIVIDE BY 16
0294          CLA,INA         A=1
0295          JSB CMPAB
0296          LDB =D2         WAS SMALLER
0297          STB SMOTH
0298 *
0312 *    UPDATE FAST AVERAGE
0313 *
0314 *
0315 *    THIS ROUTINE UPDATES A RUNNING AVERAGE BY THE METHOD
0316 *
0317 *    RAVG = (1.0 - FACTOR) * RAVG + FACTOR * NEWVAL
0318 *
0319 *    (RAVG = RAVG + FACTOR *(NEWVAL - RAVG)
0320 *
0321 *    THIS HAS AN EXPONENTIAL TIME RESPONSE SIMILAR TO AN R-C FILTER
0322 *
0323 *
0324 *    USE FACTOR = 1/2     GIVES TIME CONSTANT OF 2 BEATS
0325 *
0326 *    AND SIMPLIFY TO  RAVG=(RAVG+NEWVAL) / 2
0327 *
0328          LDB FDAVG
0329          ADB DMIN        DIAST
0330          CLE,ERB         DIV BY 2 ASSUME DATA IS POSITIVE
```

```
0331         STB FOAVG
0332 *
0333         SPC 2
0334 *
0335 *   UPDATE SLOW AVERAGE
0336 *
0337 *     TIME CONSTANT IS FASTER FOR SMOOTHER DATA
0338 *        THIS GIVES FASTER RESPONSE TO A STEP CHANGE
0339 *
0340 *
0341 *
0342 *
0343 *   THIS ROUTINE UPDATES A RUNNING AVERAGE BY THE METHOD
0344 *
0345 *   RAVG = (1.0 - FACTOR) * RAVG + FACTOR * NEWVAL
0346 *
0347 *   (RAVG = RAVG + FACTOR *(NEWVAL - RAVG)
0348 *
0349 *   THIS HAS AN EXPONENTIAL TIME RESPONSE SIMILAR TO AN R-C FILTER
0350 *
0351 *
0352 *     USE FACTOR = 1/SMOTH,     GIVES TIME CONSTANT OF 2 BEATS
0353 *                              FOR SMOOTHEST DATA
0354 *                         (98% STEP RESPONSE IN 8 BEATS)
0355 *              SMOTH=16 GIVES 98% STEP RESPONSE IN 62 BEATS
0356 *
0357         LDA SDAVG
0358         CMA,INA
0359         ADA DMIN      DIAST-SLOW AVG
0360         CLB
0361         SSA
0362         CCB           EXTEND NEG SIGN
0363         DIV SMOTH     DIAST=AVG/SMOTH
0364         ADA SDAVG     TRUNCATED, NOT ROUNDED
0365         STA SDAVG
0366 *
0367 *
0368 *
0369 *SIMILARLY, UPDATE MEAN SLOW AVERAGE
0370 *
0371 *
0372 *
0373         LDA SMAVG
0374         CMA,INA
0375         ADA BMAVG     MEAN RUNNING AVG - MEAN SLOW AVG
0376         CLB
0377         SSA
0378         CCB           EXTEND NEG SIGN
0379         DIV SMOTH     NEW = AVG/SMOTH
0380 *
0381         ARS           DIV BY 2
0382 *
0383         ADA SMAVG     TRUNCATED, NOT ROUNDED
0384         STA SMAVG
0385 *
0386 *
0518 *   SET MIN FOR NEXT TIME
0519 *
0520         LDA MAXM
0521         STA DMIN
0522         JMP GMEAN
0523         HED                 NEXT DIASTOLIC VALUE SEARCH
0524 *
0525 *
0526 DIASS LDB DMIN
0527         CPB MAXM      FIRST TIME?
0528         JMP FTDIA     YES!
0529 *
0530         JSB CHPAB           NEW MIN?
0531 *
0532         JMP GMEAN     NO
0533 *
0534         STA DMIN      YES
0535         JMP GMEAN
0536 *
0539 *   FIRST TIME INTO DIASTOLIC REGION
0540 *        TAKE PREVIOUS MAX AS SYSTOLIC FOR THIS BEAT
0541 *        RESET OFFSET
0542 *        RESET FOR NEXT TIME
```

```
0543    *
0544    *
0545    *
0546    *
0547    FTDIA EQU *         FIRST TIME DIASTOLIC
0548    *
0549    *   SET DIASTOLIC TO CURRENT VALUE
0550        STA DMIN
0551    *
0554    *
0555    *
0556    *
0557    *   EVALUATE SMOOTHNESS OF CURRENT BEAT COMPARED TO FAST AVG.
0558    *
0559        LDB FSAVG       SYST AVG
0560        CMB,INB
0561        ADB SMAX        SYST=FAST AVG
0562    *
0563        SSB             ABS VALUE
0564        CMB,INB
0565    *
0566    *   SCALE SMOOTHNESS (NOT LESS THAN 2)
0567    *
0568        LSR 4           DIVIDE BY 16
0569        CLA,INA         A=1
0570        JSB CMPAB
0571        LDB =D2         WAS SMALLER
0572        STB SMOTH
0573    *
0587    *   UPDATE FAST AVERAGE
0588    *
0589    *
0590    *   THIS ROUTINE UPDATES A RUNNING AVERAGE BY THE METHOD
0591    *
0592    *   RAVG = (1.0 - FACTOR) * RAVG  +  FACTOR * NEWVAL
0593    *
0594    *   (RAVG = RAVG + FACTOR *(NEWVAL - RAVG)
0595    *
0596    *   THIS HAS AN EXPONENTIAL TIME RESPONSE SIMILAR TO AN R-C FILTER
0597    *
0598    *
0609    *
0610    *   UPDATE SLOW AVERAGE
0611    *
0612    *   TIME CONSTANT IS FASTER FOR SMOOTHER DATA
0613    *       THIS GIVES FASTER RESPONSE TO A STEP CHANGE
0614    *
0615    *
0616    *
0617    *
0618    *   THIS ROUTINE UPDATES A RUNNING AVERAGE BY THE METHOD
0619    *
0620    *   RAVG = (1.0 - FACTOR) * RAVG  +  FACTOR * NEWVAL
0621    *
0622    *   (RAVG = RAVG + FACTOR *(NEWVAL - RAVG)
0623    *
0624    *   THIS HAS AN EXPONENTIAL TIME RESPONSE SIMILAR TO AN R-C FILTER
0625    *
0626    *
0627    *   USE FACTOR = 1/SMOTH,    GIVES TIME CONSTANT OF 2 BEATS
0628    *                              FOR SMOOTHEST DATA
0629    *                            (98% STEP RESPONSE IN 6 BEATS)
0630    *               SMOTH=16 GIVES 98% STEP RESPONSE IN 62 BEATS
0631    *
0632        LDA SSAVG
0633        CMA,INA
0634        ADA SMAX        SYST=SLOW AVG
0635        CLB
0636        SSA
0637        CCB             EXTEND NEG SIGN
0638        DIV SMOTH       SYST-AVG/SMOTH
0639        ADA SSAVG       TRUNCATED, NOT ROUNDED
0640        STA SSAVG
0641    *
0642    *
0643    *
0644    *SIMILARLY, UPDATE MEAN SLOW AVERAGE
0645    *
0646    *
```

```
0647  *
0648       LDA SMAVG
0649       CMA,INA
0650       ADA BMAVG      MEAN RUNNING AVG - MEAN SLOW AVG
0651       CLB
0652       SSA
0653       CCB            EXTEND NEG SIGN
0654       DIV SMOTH      NEW = AVG/SMOTH
0655  *
0656       ARS            DIV BY 2 TO SLOW AVG
0657  *
0658       ADA SMAVG      TRUNCATED, NOT ROUNDED
0659       STA SMAVG
0660  *
0792  *    SET MAX FOR NEXT TIME
0793  *
0794       LDA MIN#
0795       STA SMAX
0796  *
0797  *
0807  *                   20 * 20 MSEC = 0.4 SEC
0808  *
0809  GMEAN LDA BMAVG     OLD AVG
0810       CMA,INA
0811       ADA PDATA      NEW VALUE
0812       ARS,ARS
0813       ARS,ARS        DIVIDE BY 16
0814  *
0815       SSA,RSS        DITHER FOR VALUES BETWEEN 0 AND 15
0816       INA
0817  *
0818       ADA BMAVG
0819       STA BMAVG
0820  *
0821       JMP NEXT       NEXT DATA VALUE
0822       SPC 4
0823  *
0824  *
0825  MIN# DEC -32768
0826  MAX# DEC 32767
0827  TMOUT DEC #250      SET FOR 5 SECONDS AT 50 HZ
0828  *
0829  *
0830  *
0831  *
0832  *
0833       HED CMPAB ROUTINE
0834  *
0835  *
0836  *
0837  *
0838  *    THIS ROUTINE RETURNS TO P+1 IF A = OR > B
0839  *    THIS ROUTINE RETURNS TO P+2 IF A < B
0840  *
0841  CMPAB NOP
0842       CMB,INB        NOTE!
0843       ADB A          E AND O REGISTERS LOST!
0844       CMB,SSB,INB,RSS
0845       ISZ CMPAB
0846       ADB A
0847       JMP CMPAB,I
0848  *
0849       END
```

What is claimed is:

1. Apparatus for processing an input signal, comprising.

a signal input terminal, first means for deriving at its output a first signal representative of an average of at least some of the values of a signal applied to its input, means providing a value at the input of said first means representing the value of the signal at said signal input terminal, second means for deriving at its output a second signal representative of the absolute value of the relative deviation between the values represented by signals applied to first and second inputs thereof, means for providing a value at the first input of said second means representing the value at said signal terminal, and means providing a value at the second input of said second means representing the signal value at the output of said first means, third means for deriving at its output of third signal representative of the difference between the values represented by signals coupled to different inputs thereof, a signal output terminal having means for maintaining the value of a signal applied to it, means providing a value at one input of said third means representing the value at said signal input terminal, and means providing a value at the other input of said third means representing the value at said signal output terminal, fourth means coupled to the outputs of said second and third means for deriving a fourth signal at its output representing a portion of the value represented by the third signal, the portion being larger when said second signal becomes smaller and smaller when said second signal becomes larger, control means coupled to said fourth means for changing the value represented by the signal at said signal output by an amount proportional to said fourth signal, and means for selectively activating said first, second, third and fourth means.

2. Apparatus as set forth in claim 1 having an information signal input and a peak detecting means coupled between said information signal input and said signal input.

3. Apparatus as set forth in claim 2 wherein means are provided for producing a signal indicative of the occurrence of a new peak value in the signal applied to said signal input, and means applying said latter signal to said activating means whereby the value represented by the signal at said signal output may be changed in response to each new peak value applied to said signal input independent of time.

4. Apparatus as set forth in claim 2 wherein means are provided for applying a signal representative of blood pressure variations with time to said information signal input and wherein said peak detecting means provides a signal representative of the systolic peaks of blood pressure in such manner as to include the effects of respiratory undulations and false peaks due to artifacts and noise, when present.

5. Apparatus as set forth in claim 2 wherein means are provided for applying a signal representative of blood pressure variations with time to said information signal input and wherein said peak detecting means provides a signal representative of the diastolic peaks of blood pressure in such manner as to include the effects of respiratory undulations and false peaks due to artifacts and noise, when present.

6. An apparatus as set forth in claim 2 wherein said first means derives a first signal that represents an exponential average of the peaks of the signal at said signal input.

7. Apparatus as set forth in claim 1 where means are provided for initializing the apparatus by setting the initial value represented by the signal at said signal output and the initial value represented by said first signal at selected values.

8. Apparatus for processing an input signal representing the variation in blood pressure with time in which there are systolic and diastolic peaks and peaks due to noise as well as undulations due to respiration in such manner as to produce an output signal having a value representing one of the systolic and diastolic peak pressures in which the effects of noise and respiration undulations are reduced, comprising an input to which a signal representing the variation in blood pressure with time may be applied, first means coupled to said input for deriving a first signal approximately representing the peaks of said one of the systolic and diastolic pressures of a blood pressure signal when present in such manner that the effects of the undulations and noise may be present, second means coupled to the output of said first means for deriving a second signal representing an average of some previous peaks represented by said first signal, third means responsive to said first and second signals for deriving a control signal representative of the absolute value of the deviation between the first and second signals, an output from which an output signal may be derived, fourth means responsive to said first signal and a signal at said output for providing a fourth signal representative of the difference in value between the value represented by the first signal and the value represented by the signal at said output, and means for changing the signal at said output by a portion of the value represented by said fourth signal, the said portion increasing as said control signal gets smaller and decreasing as said control signal gets larger.

9. A method of processing an input signal representing variations in systolic or diastolic blood pressures in such manner as to derive an output signal in which the effects of undulations contained in the input signal that are caused by respiration as well as the effects of false values contained in the input signal that are caused by noise are reduced, comprising sampling the amplitude of the input signal at successive instants of time, deriving an average of the values of at least some of the prior samples, deriving a first difference between the value of each sample and the value of the average amplitude of samples prior to it, determining a second difference between the value of each sample and the value of the output signal, and changing the value represented by the output signal in the direction of the input signal by a portion of the second difference that increases as the first difference decreases and decreases as the first difference increases.

10. A method of processing an input signal in such manner as to derive an output signal which is more responsive to a slow change in value of the input signal than it is to a fast change in the value of the input signal, comprising sampling the amplitude of the input signal at successive instants of time, deriving an average of the values of at least some of the prior samples, deriving a first difference between the value of each sample and the value of the average amplitude of samples prior to it, determining a second difference between the value of each sample and the value of the output signal, and changing the value represented by the output signal in the direction of the input signal by a portion of the second difference that increases as the first difference decreases and decreases as the first difference increases.

* * * * *